United States Patent [19]

Elliott et al.

[11] Patent Number: 5,192,533

[45] Date of Patent: * Mar. 9, 1993

[54] NONIRRITATING ANTITARTAR AND ANTIPLAQUE ORAL COMPOSITIONS

[75] Inventors: David L. Elliott, Hawthorne; Esther Patrick, Ridgefield, both of N.J.

[73] Assignee: Chesebrough-Pond's USA Co., Division of Conopco, Inc., Greenwich, Conn.

[*] Notice: The portion of the term of this patent subsequent to Apr. 30, 2008 has been disclaimed.

[21] Appl. No.: 858,374

[22] Filed: Mar. 25, 1992

[51] Int. Cl.$^5$ .......................... A61K 7/16; A61K 7/22
[52] U.S. Cl. .......................... 424/54; 424/49; 424/52; 424/57
[58] Field of Search ........................ 424/49-58

[56] References Cited

U.S. PATENT DOCUMENTS

| | | | |
|---|---|---|---|
| 4,022,880 | 5/1977 | Vinson et al. | 424/49 |
| 4,025,616 | 5/1977 | Haefele | 424/52 |
| 4,110,083 | 8/1978 | Benedict | 424/54 |
| 4,157,387 | 6/1979 | Bennedict | 424/54 |
| 4,980,153 | 12/1990 | Jackson et al. | |
| 5,011,682 | 4/1991 | Elliott et al. | 424/52 |
| 5,043,154 | 8/1991 | Gaffar et al. | |

FOREIGN PATENT DOCUMENTS 0397452  11/1990  European Pat. Off.

OTHER PUBLICATIONS

B. E. Beacham et al., Journal of the American Academy of Dermatology, vol. 22, pp. 1029–1032, 1990.
G. Kowitz et al., Oral Surg. Oral Med. Oral Pathol., vol. 70, pp. 529–536 (1990).

*Primary Examiner*—Shep K. Rose
*Attorney, Agent, or Firm*—Milton L. Honig

[57] ABSTRACT

A method and composition for controlling tartar and plaque formation in the mouth is reported which has a relatively low irritation to the mucosae. The oral composition includes (1) a hypophosphite-containing cotelomer in an amount effective for controlling tartar; and (2) an antibacterial agent selected from the group consisting of diphenyl ethers, bis-biguanides, halogenated carbanilides and salicylamides.

17 Claims, No Drawings

NONIRRITATING ANTITARTAR AND ANTIPLAQUE ORAL COMPOSITIONS

BACKGROUND OF THE INVENTION

1. Field of the Invention

The invention relates to new compositions and a method for control of tartar and plaque formation on teeth.

2. The Related Art

Compositions with active ingredients against tartar and plaque have been disclosed in the literature. In U.S. Pat. No. 4,894,220 (Nabi et al.) is described an oral composition whose active ingredients are 2,4,4'-trichloro-2'-hydroxydiphenyl ether (hereinafter known as triclosan), alkali metal pyrophosphate and a synthetic anionic polymeric polycarboxylate (e.g. Gantrez ®). Pyrophosphate and polycarboxylate provide the antitartar effect while the triclosan attacks plaque. See also U.S. Pat. No. 5,043,154 (Gaffar et al.) and U.S. Pat. No. 4,980,153 (Jackson et al.). Somewhat similar is EP 0 397 452 (Ibrahim et al.) which combines tripolyphosphate salts as the antitartar agent along with triclosan.

Although pyrophosphates are cost-effective, they have been shown to have an irritating effect on human skin and oral soft tissue. Recent reports in the dental literature suggest that pyrophosphate-containing dentifrices are harsher to oral tissues than other products. For example, B. E. Beacham et al. (*Journal of the American Academy of Dermatology* 22, p. 1029–1032 [1990]) found that use of pyrophosphate-containing antitartar toothpastes resulted in perioral erythema after 4 to 14 days. This condition was found to be caused by the pyrophosphate. G. Kowitz et al. (*Oral Surg. Oral Med. Oral Pathol.* 70, p. 529–536 [1990]) also studied the effects of medium and low doses of both flavoring agents and pyrophosphate in toothpastes, and found that higher rates of mucosal reactions such as ulceration, sloughing, and erythema were caused predominantly by the pyrophosphate Other common ingredients such as detergents (sodium lauryl sulfate) and flavoring agents are known in the art to cause irritation to skin and oral tissue. The result of such irritation is health risks upon long-term exposure or, at minimum, poor consumer perception due to burning sensation, irritation and flaking/dryness associated with use of such products.

In addition, products having combinations of pyrophosphate and triclosan, though desirable for their oral benefit, are also irritating to skin tissue. Zinc/triclosan combinations give similar gum health benefit but zinc levels must be held below about 2% because of its undesirable metallic taste and astringency. Clearly, combinations of agents potentially give desirable benefits but are limited by safety concerns and aesthetic effects of common commercial agents.

Accordingly, it is an object of the present invention to provide compositions for use in the oral cavity having both improved antitartar and antiplaque effectiveness.

A further object of the present invention is to provide compositions for use in the oral cavity that control tartar and plaque formation but are also nonirritating on the mucosal areas of the mouth.

A still further object of the present invention is to provide a method for controlling tartar and plaque formation that results in a less irritating application than heretofore achievable.

These and other objects of the present invention will become more apparent by consideration of the following summary, detailed description and Examples.

SUMMARY OF THE INVENTION

An oral composition is provided comprising:

(i) a polymer present in an effective amount to control build-up of tartar, said polymer having the formula I:

wherein A is a random polymeric residue comprising at least one unit of structure II,

and at least one unit of structure III, different from a unit of structure II,

and B is hydrogen or a residue A; m and n are integers sufficient to provide polymer of weight averaged molecular weight ranging from about 400 to about 5000; m and n in residue A may each be the same or different from respective m and n in residue B; R is an —OX, where X is selected from the group consisting of hydrogen, alkali metal, alkaline earth metal, transition metal, ammonium, lkyl amine, alkanolammonium residues and mixtures thereof; $R_1$, $R_2$, $R_3$ and $R_4$ are hydrogen, methyl, ethyl radicals or combinations thereof; and (ii) an effective amount of an antibacterial agent for destroying microorganisms selected from the group consisting of diphenyl ethers, bis-biguanides, halogenated carbanilides and salicylamides.

A method is also provided for inhibiting tartar and plaque formation in the mouth by treating the oral cavity with a composition as defined above.

DETAILED DESCRIPTION

Now it has been found that combinations of hypophosphite-containing cotelomers in combination with certain antibacterial agents provide effective tartar and plaque control on teeth while minimizing mucosal irritation normally associated with such active compounds.

Hypophosphite-containing cotelomers of the present invention have three essential components. There must be present a monocarboxylic acid monomer, a dicarboxylic acid monomer, and a hypophosphite, which when reacted will form polymers of this invention.

The general structure of the polymers of this invention are as follows:

 (I)

wherein A is a random polymeric residue comprising at least one unit of structure II,

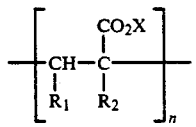 (II)

and at last one unit of structure III, different from a unit of structure II,

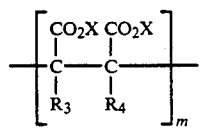 (III)

and B is hydrogen or a residue A; m and n are integers sufficient to provide polymer of weight averaged molecular weight ranging from about 400 to about 5000; m and n in residue A may each be the same or different from respective m and n in residue B; R is an —OX, where X is selected from the group consisting of hydrogen, alkali metal, alkaline earth metal, transition metal, ammonium, alkyl amine, alkanolammonium residues and mixtures thereof; $R_1$, $R_2$, $R_3$ and $R_4$ are hydrogen, methyl, ethyl radicals or combinations thereof.

Polymers forming the structure II will have a single carboxylic acid or salt group. There will be anywhere from 3 to 7 carbon atoms for this structure. Suitable monomers include acrylic acid, methacrylic acid, alpha-substituted alkyl acrylic acids, and beta-carboxyalkyl acrylates.

Monomers that form structure III will have at least two carboxylic acid groups and may range from 4 to 7 carbon atoms in size. Suitable monomers include maleic acid, fumaric acid, itaconic acid, mesaconic acid, citraconic acid, their anhydrides or salts.

Specific salts of the mono- and di- carboxylic monomers may be those including the counterions of sodium, potassium, calcium, tin, strontium, zinc, copper, ammonium, $C_2$-$C_9$ alkanolammonium, $C_1$-$C_8$ alkyl amine and mixtures thereof. Strontium and zinc are particularly preferred counterions.

Most preferred are copolymers formed from acrylic acid and maleic acid.

Polymers of this invention are telomeric. Sodium hypophosphite is present in the polymerization medium to control molecular weight and to be incorporated into the backbone as mono- or disubstituted hypophosphite groups. These groups may be incorporated at the chain end or between monomer units in the chain. Typically, 70-90% of the total hypophosphite groups will be disubstituted. These groups are essential for the enhanced benefit of the polymers of this invention.

Molar ratio of total monomer to hypophosphite of the raw components before polymerization may range from about 40:1 to about 1:1, preferably from about 20:1 to about 4:1, optimally between about 16:1 to about 7:1. Lower ratios of monomer to hypophosphite generally result in lower polymer molecular weight and higher levels of incorporation of hypophosphite in the polymers.

Dicarboxylic monomers should be present in amounts in the copolymer ranging from about 10 to about 95 mole percent, preferably from about 20 to about 75 mole percent. Molar ratios of monocarboxylic monomer to dicarboxylic monomer should preferably be from about 5:1 to about 1:5, optimally between about 4:1 to about 1:1.

Polymers of this invention should have a molecular weight in the range between about 400 to about 5000, with a range of about 600 to about 2500 being preferred. These polymers will be present in the oral compositions in amounts ranging from about 0.01 to about 10% by weight, preferably about 0.4 to about 7%, optimally between about 1 to about 5%.

According to the present invention there will also be present an antibacterial agent in amounts sufficiently effective to control plaque formation on the teeth. Concentration levels of this material will range from about 0.001 to about 10% by weight, preferably between about 0.01 and 1% by weight, optimally between about 0.1 and 0.5% by weight. The antibacterial agent will be selected from the group consisting of diphenyl ethers, bis-biguanides, halogenated carbanilides and salicylamides.

The term diphenyl ethers refers to substances of the general formula (1):

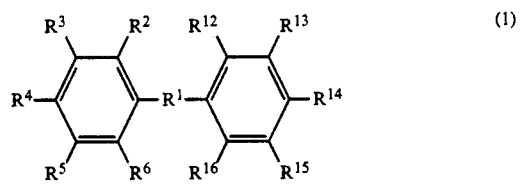 (1)

in which $R^1$ is oxygen, sulfur or an alkylene group of from one to six carbon atoms and each of $R^2$ through $R^6$ and $R^{12}$ through $R^{16}$ is hydrogen, hydroxyl or a halogen.

Examples of compounds of formula (I) include, for example, 5,5'-dichloro-2,2'-dihydroxydiphenylmethane; 2,2-dihydroxy-3,5,6,3',5',6'-hexachlorodiphenylmethane; 3,3'-dibromo-5,5'-di-chloro-2,2'-dihydroxydiphenyl ether and 2,4,4'-trichloro-2'-hydroxydiphenyl ether (triclosan); of which triclosan is particularly preferred.

Other suitable antibacterial compounds are the bis-biguanides having the formula (2):

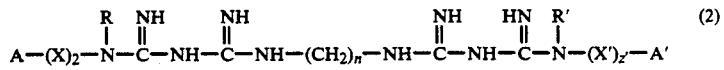 (2)

wherein A and A' each represent either (1) a phenyl radical which optionally is substituted by an alkyl or alkoxy group containing from 1 to about 4 carbon atoms, a nitro group or a halogen atom; (2) an alkyl group containing from 1 to about 12 carbon atoms; or (3) alicyclic groups containing from 4 to about 12 carbon atoms;

X and X' each represent an alkylene radical containing from 1 to 3 carbon atoms;

z and z' each can be either 0 or 1:

R and R' each represent either hydrogen, an alkyl radical containing from 1 to about 12 carbon atoms or an aralkyl radical containing from 7 to about 12 carbon atoms;

n is an integer from 2 to 12 inclusive; and wherein the polymethylene chain $(CH_2)_n$ may optionally be interrupted by oxygen or sulfur atoms, aromatic nuclei, etc.

The salts of the above compounds are especially desirable. Water-soluble salts include the acetate, the hydrochloride, and especially the gluconate salt of the above compounds.

Examples of bis-biguanide compounds useful in the present invention include the following:

1,6-bis-(2-ethylhexylbiguanidohexane) dihydrochloride;
1,6-di-($N_1$, $N_1'$-phenyldiguanido-$N_5$, $N_5'$)-hexane tetrahydrochloride;
1,6-di-($N_1$, $N_1'$-phenyl-$N_1$,$N_1'$-methyldiguanido-$N_5$,$N_5'$)-hexane dihydrochloride;
1,6-di-($N_1$,$N_1'$-o-chlorophenyldiguanido-$N_5$,$N_5'$)-hexane dihydrochloride;
1,6-di($N_1$,$N_1'$,-2,6-dichlorophenyldiguanido-$N_5$,-$N_5'$)-hexane dihydrochloride;
1,6-di($N_1$,$N_1'$-β-(p-methoxyphenyl)-diguanido-$N_5$,$N_5'$)-hexane dihydrochloride;
1,6-di($N_1$,$N_1'$-α-methyl-β-phenyldiguanido-$N_5$, $N_5'$)-hexane dihydrochloride;
1,6-di($N_1$,$N_15$,$N_5'$)-hexane dihydrochloride;
w:w'-di-($N_1$,$N_1$-phenyldiguanido-$N_5$, $N_5'$)di-n-propylether dihydrochloride;
w:w-di($N_1$,$N_1'$-p-chlorophenyldiguanido-$N_5$,$N_5'$)-di-n-propylether tetrahydrochloride;
1,6-di($N_1$,Nhd 1'-2,4,5,5,$N_5'$) hexane tetrahydrochloride;
1,6-di($N_1$,$N_1'$-p-methylphenyldiguanido-$N_5$,$N_5'$)-hexane dihydrochloride;
1,6-di($N_1$,Nhd 1'-2,4,5,5,$N_5'$)hexane tetrahydrochloride;
1,6-di-($N_1$,$N_1$-α-(p-chlorophenyl)ethyldiguanido-$N_5$,$N_5'$)hexane dihydrochloride;
w:w'-di($N_1$,$N_1'$-p-chlorophenyldiguanido-$N_5$,$N_5'$)m-xylene dihydrochloride;
1-12-di-($N_1$,$N_1'$p-chlorophenyldiguanido-$N_5$,$N_5'$)-dodecane dihydrochloride;
1,10-di($N_1$,$N_1'$-phenyldiguanido-$N_5$,$N_5'$)-decane tetrachloride;
1,12-di($N_1$,$N_1'$-phenyldiguanido-$N_5$,$N_5'$)-dodecane tetrahydrochloride;
1,6-di($N_1$,$N_1'$-o-chlorophenyldiguanido-$N_5$,$N_5'$)hexane dihydrochloride;
1,6-di($N_1$,$N_1'$-p-chlorophenyldiguanido-$N_5$,$N_5'$)-hexane tetrahydrochloride;
ethylene bis(1-tolyl biguanide);
ethylene bis(p-tolyl biguanide);
ethylene bis(3,5-dimethylphenyl biguanide);
ethylene bis(p-tert-amylphenyl biguanide);
ethylene bis(nonylphenyl biguanide);
ethylene bis(phenyl biguanide);
ethylene bis(N-butylphenyl biguanide);
ethylene is(2,5-diethoxyphenyl biguanide);
ethylene bis(2,4-dimethylphenyl biguanide);
ethylene bis(o-diphenylbiguanide);
ethylene bis(mixed amyl naphthyl biguanide);
N-butyl ethylene bis(phenyl biguanide);
trimethylene bis(o-tolyl biguanide);
N-butyl trimethylene bis(phenylbiguanide);
tetramethylene bis(1-tolyl biguanide);
the specific compounds disclosed in U.S. Pat. No. 2,863,919, Birtwell et al, (Dec. 9, 1958);
the specific compounds disclosed in U.S. Pat. No. 3,468,898, Cutler et al, (Sep. 23, 1969);
the specific compounds disclosed in U.S. Pat. No. 4,059,687, Bauman (Nov. 22, 1977); and
the corresponding pharmaceutically acceptable salts of all of the above such as the acetates, gluconates, hydrochlorides, hydrobromides, citrates, bisulfites, hydrofluorides, polymaleates, N-coconutalkyl sarcosinates, phosphites, hypophosphites, perfluorooctanoates, silicates, sorbates, salicylates, maleates, tartrates, fumarates, ethylenediaminotetraacetates, iminodiacetates, cinnamates, thiocyanates, arginates, pyromellitates, tetracarboxybutyrates, benzoates, glutarates, monofluorophosphates and perfluoropropionates.

The most preferred bis-biguanide compound is 1,6-di($N_1$,$N_1'$-p-chlorophenyldiguanido-$N_5$,$N_5'$)hexane, known more commonly as chlorhexidine and salts thereof.

Halogenated carbanilides may also be suitable as the antibacterial agent. Preferred examples of this class include 3,4,4'-trichlorocarbanilide; 3-trifluoromethyl-4,4'-dichlorocarbanilide; and 3,3',4-trichlorocarbanilide.

Further suitable antibacterial agents for purposes of this invention are the salicylamides having the formula (3):

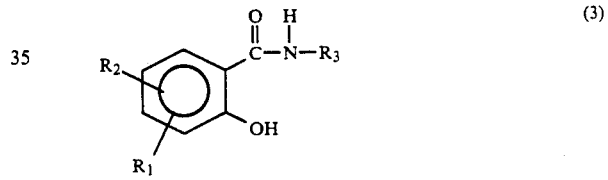

wherein the lipophilicity imparting substituents —$R_1$ and —$R_2$ which impart an octanol/water distribution function of about 3.0 to about 10 to the compound are hydrogen, normal or branched chain or cyclic or fused ring polycyclic or non-fused ring polycyclic alkyl, alkenyl, alkynyl, aryl or heteroaryl groups optionally containing further substituents thereon, the —$R_1$ and —$R_2$ substituents comprising up to about 30 carbon atoms when taken together either attached directly to the phenyl ring provided with an amido and a hydroxyl group in an ortho orientation with respect to each other or attached to said phenyl ring through a

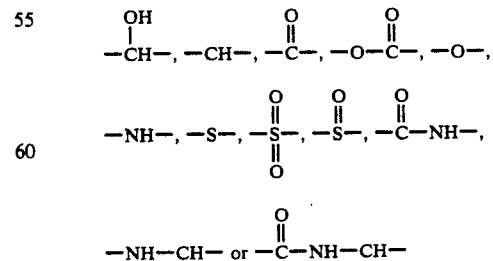

group with the proviso that —$R_1$ and —$R_2$ are not both hydrogen and wherein —$R_3$ is selected from the group consisting of thiazol-2-yl, benzothiazol-2-yl and $R_4$-substituted phenyl wherein $R_4$ is selected from the group consisting of —OH, —COOH, the tautomeric pair

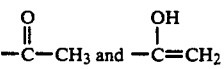

—$CH_2COOH$, —$COOCH_3$, —$COOC_2H_5$, —$CH_2COOCH_3$, —$CH_2COOC_2H_5$, —$NO_2$, and $CX_1X_2X_3$ wherein $X_1$, $X_2$ and $X_3$ are halogen atoms, with halogen atoms directly attached to any aromatic ring being absent in the compounds.

Preferred salicylamides are those having the structure (3a):

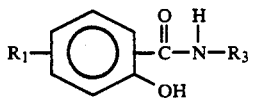

(3a)

wherein
$R_1$ is n-decanoyl, and $R_3$ is p-nitrophenyl;
$R_1$ is n-octanoyl, and $R_3$ is p-trifluoromethylphenyl;
$R_1$ is a n-octanoyl, and $R_3$ is m-trifluoromethylphenyl;
$R_1$ is n-hexyl, and $R_3$ is p-nitrophenyl;
$R_1$ is n-butyl, and $R_3$ is m-trifluoromethylphenyl;
$R_1$ is n-nonanoyl, and $R_3$ is m-carbethoxyphenyl;
$R_1$ a n-decanoyl, and $R_3$ is benzothiazol-2-yl;
$R_1$ is n-hexadecanoyl, and $R_3$ is thiazol-2-yl; and
$R_1$ is n-decanoyl, the —OH group is replaced by acryloyloxy and $R_3$ is p-nitrophenyl.

Oral compositions of the present invention may be in the form of a dental paste, gel, tablet, powder or mouthwash. A carrier medium will usually be present as a vehicle for delivery of the active ingredients. Where the oral composition is in the form of a paste or gel, the carrier preferably will be a hydroxylic material such as water, polyols and combinations thereof.

Polyols, sometimes referred to as humectants, include glycerol, sorbitol, propylene glycol, lactitol, xylitol, polypropylene glycol, polyethylene glycol, hydrogenated corn syrup and mixtures thereof. Particularly preferred as the carrier is a liquid mixture of 3-30% water, 0-80% glycerol and 20-80% sorbitol. Generally the amount of carrier will range from about 25 to 99.9% by weight, preferably from about 70 to 95% by weight.

When the oral compositions are in the form of a toothpaste or gel there will typically be included a natural or synthetic thickening agent in an amount from 0.1-10%, preferably about 0.5-5% by weight. Thickeners may include crosslinked polyacrylates (e.g. Carbopol 940, ex B.F. Goodrich) hydroxypropyl methyl cellulose, hydroxyethyl cellulose, sodium carboxymethyl cellulose, xanthan gum, tragacanth gum, karaya gum, arabic gum, Irish moss, starch, alginates and carrageenans. The amount of thickening agent will generally be between about 0.1 and 10% by weight.

Surfactants are normally also included in the oral compositions of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to 5% by weight.

When in the form of a toothpaste or gel, the oral compositions will normally include an abrasive. Abrasives may be selected from water-insoluble alkali or alkaline earth metal salts of metaphosphate, calcium carbonate, aluminates and silicates. Especially preferred are silicate, dicalcium phosphate and calcium carbonate. Amounts of the abrasive will range from about 5% to about 80% by weight.

For anticaries protection, a source of fluoride ion will normally be present in the oral compositions. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anticaries agent will be present in an amount from about 0.05 to about 3% by weight, preferably 0.5 to 1% by weight.

Flavors that are usually present in the oral compositions are those based on oils of spearmint and peppermint. Examples of other flavoring materials include menthol, clove, wintergreen, eucalyptus and aniseed. Flavors may range in concentration from 0.1 to 5% by weight.

Sweetening agents such as saccharin, sodium cyclamate, aspartame, sucrose and the like may be included at levels from about 0.1 to 5% by weight.

Other additives may also be incorporated into the oral compositions including preservatives, silicones, other synthetic or natural polymers for example Gantrez S-97 ®, and antigingivitis actives.

The following Examples will more fully illustrate the embodiments of this invention. All parts, percentages and proportions referred to herein and in the appended claims are by weight of the total composition unless otherwise stated.

EXAMPLE 1

An evaluation was performed between Cotelomer AM-C and pyrophosphate to determine the difference in their irritation properties. Cotelomer AM-C is an acrylate/maleate copolymer of molar ratio 1.5:1, having a monomer/hypophosphite ratio of 8:1 and a molecular weight of 1200; this cotelomer and related ones are described in U.S. Pat. No. 5,011,682 (Elliott et al) herein incorporated by reference. The irritancy test was conducted over a 24-hour exposure period and evaluated in a multiracial panel of 10 subjects between ages 29 and 53 years. A 5% actives solution of the copolymer was used, as was a 50:50 mixture of tetrapotassium and tetrasodium pyrophosphate in water (5% total actives as pyrophosphate). Patches were applied to the upper arm. Test solutions were held in contact with the skin via an occlusive patch backed with Scanpor tape to adhere the device to the skin. Each patch contained 0.1 ml of test solution. Patches were removed after a 24-hour exposure period. The test sites were evaluated at 6, 24 and 48 hours after patch removal. Observations were made by a trained examiner under consistent lighting. Sites were evaluated for erythema and edema using the following scale:

| No visible response, negative | 0 |
|---|---|
| Very slight | 0.5 |
| Definite | 1 |
| Well-developed | 2 |
| Severe | 3 |

Table I gives a comparison of the irritation for the two agents. The patches with AM-C were found to be nonirritating in this test. The pyrophosphate was found to be mildly irritating.

TABLE I

|  | Pyrophosphate | | Cotelomer AM-C | |
| --- | --- | --- | --- | --- |
|  | Erythema | Edema | Erythema | Edema |
| 6-Hour Average | 1 | 0.5 | 0 | 0 |
| 24-Hour Average | 0.4 | 0.1 | 0 | 0 |
| 48-Hour Average | 0.1 | 0 | 0 | 0 |

EXAMPLE 2

The following toothpaste formulations were prepared:

|  |  | Active Ingredient(s) |
| --- | --- | --- |
| A | Placebo | None |
| B | Triclosan | 0.3% Triclosan |
| C | Pyrophosphate | 3.3% Pyrophosphate |
| D | AM-C | 5.0% AM-C |
| E | AM-C/Triclosan | 5.0% AM-C, 0.3% Triclosan |
| F | Pyrophosphate/Triclosan | 3.3% Pyrophosphate, 0.3% Triclosan |

TABLE II

| Ingredient | A | B | C | D | E | F |
| --- | --- | --- | --- | --- | --- | --- |
| Polyol II[1] | 45.00 | 45.00 | 45.00 | 45.00 | 45.00 | 45.00 |
| Deionized Water | 29.11 | 28.81 | 23.51 | 18.19 | 17.89 | 23.21 |
| AM-C Polymer[2] | — | — | — | 10.92 | 10.92 | — |
| Abrasive Silica[3] | 10.00 | 10.00 | 10.00 | 10.00 | 10.00 | 10.00 |
| Thickening Silica[4] | 8.00 | 8.00 | 8.00 | 8.00 | 8.00 | 8.00 |
| Polyethylene Glycol[5] | 5.00 | 5.00 | 5.00 | 5.00 | 5.00 | 5.00 |
| TKPP[6] | — | — | 3.10 | — | — | 3.10 |
| TSPP[7] | — | — | 2.50 | — | — | 2.50 |
| Sodium Lauryl Sulfate[8] | 1.50 | 1.50 | 1.50 | 1.50 | 1.50 | 1.50 |
| Carboxymethyl Cellulose[9] | 0.50 | 0.50 | 0.50 | 0.50 | 0.50 | 0.50 |
| Titanium Dioxide[10] | 0.50 | 0.50 | 0.50 | 0.50 | 0.50 | 0.50 |
| Triclosan[11] | — | 0.30 | — | — | 0.30 | 0.30 |
| Sodium Fluoride[12] | 0.214 | 0.214 | 0.214 | 0.214 | 0.214 | 0.214 |
| Sodium Saccharin[13] | 0.18 | 0.18 | 0.18 | 0.18 | 0.18 | 0.18 |
| TOTAL | 100.0 | 100.0 | 100.0 | 100.0 | 100.0 | 100.0 |
| pH (25% slurry) | 6.37 | 6.30 | 8.53 | 7.88 | 7.85 | 8.52 |

[1] Supplied by Roquette (70% solids)
[2] Copolymer of acrylic acid and maleic acid; molecular weight 1200; feed ratio of acylate to maleate 1.5:1; 8:1 ratio of monomer to hypophosphite; supplied as an aqueous solution (45.8% actives)
[3] Gasil 200; supplied by Crosfield Chemicals
[4] Sident 22S; supplied by Degussa Corp.
[5] PEG-32; supplied by Union Carbide Corporation
[6] Tetrapotassium pyrophosphate; supplied by Monsanto Company
[7] Tetrasodium pyrophosphate; supplied by Monsanto Company
[8] Supplied by Stepan Chemicals as Stepanol WA-100 (99.02% actives)
[9] Supplied by Aqualon
[10] Supplied by Whittaker Chemicals
[11] Supplied by Ciba-Geigy Corporation as Irgacare MP
[12] Supplied by PhilBro Chem (99.89% solids)
[13] Supplied by PMC Specialties

EXAMPLE 3

An occlusive patch test was conducted using the procedure of Example 1 with the following modifications:

1. 14 subjects between ages 23–51 participated in the test.
2. The 6 formulations listed in Example 2 were tested.
3. 20% (W/V) dilutions of formulations A–F from Example 2 were used as the dosing solutions.
4. 0.2 mL of dosing solution was applied to each patch.
5. Fresh sets of patches were placed on the same sites of the upper arm each day for 4 consecutive days. After 23 hour exposures, the patches were removed. Sites were evaluated 1 hour after patch removal, just before application of the next set of patches. Sites which were assigned grades of 2 for erythema or 0.5 for edema were not reexposed to the test material.
6. The degree of irritancy produced by each material at each exposure was ranked. If dosing with a material was discontinued that material retained the highest or higher ranking for subsequent evaluations.

Friedman's rank sum analysis of the degree of inflammation produced by each treatment after each exposure was used to determine if there were statistically significant differences between the treatments. An experiment-wise error rate of $\alpha = 0.05$ was used to detect differences between pairs. Rankings by degree of erythema were the most sensitive parameter for detecting differences.

TABLE III
Comparison of Graded Skin Irritation

| Formulation | Rank | Summation of Ranks for Each Evaluation | | |
| --- | --- | --- | --- | --- |
|  |  | Erythema | Edema | Dryness |
| A | 2 | 33.5 | 36.0 | 37.5 |
| B | 3 | 39.0 | 40.5 | 41.5 |
| C | 5 | 66.5 | 66.5 | 60.5 |
| D | 4 | 53.0 | 54.0 | 54.5 |
| E | 1 | 33.0 | 30.0 | 32.5 |
| F | 6 | 69.0 | 67.0 | 67.5 |

NOTE:
Rank #: 1 has the least irritation; 6 has the most irritation.
The above summations are determined by assigning a relative rank of the 6 samples after the 4-day period for the 14 subjects. Thus, the maximum score attainable is 84 and the minimum is 14.

No statistically significant differences among the treatments were detected after 1 exposure. After 2 exposures the toothpaste containing pyrophosphate and triclosan (formulation F) was significantly more irritating than the placebo toothpaste (formulation A). After 3 exposures, formulation F (pyrophosphate/triclosan) was significantly more irritating than formulation E (AM-C/triclosan) and formulation A (placebo). After 4 exposures, formulation F was significantly more irritating than formulation A (placebo), formulation E (AM-C/triclosan) and formulation B (triclosan). Formulation E (AM-C/triclosan) was not significantly different than formulation A (the placebo) at any evaluation.

The general rank ordering of inflammation produced by the treatments predominant through all evaluations was:

$$E < A < B < D < C < F$$

with formulation E (AM-C/triclosan) being the most benign treatment and formulation F (pyrophosphate/triclosan) being the most severe.

In summary, toothpastes containing combinations of triclosan and polymer AM-C were surprisingly mild, having irritation levels similar to the placebo. Pyrophosphate/triclosan combinations were significantly more irritating than the AM-C/triclosan paste.

Although this invention has been described with reference to specific Examples, it will be apparent to one skilled in the art that various modifications may be made thereto which fall within its scope.

What is claimed is:

1. An oral composition comprising:
   (i) a polymer present in an effective amount to control build-up of tartar, said polymer having the formula I:

  (I)

wherein A is a random polymeric residue comprising at least one unit of structure II.

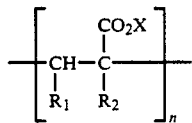  (II)

and at least one unit of structure III, different from a unit of structure II,

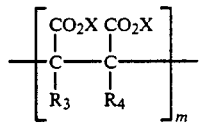  (III)

and B is hydrogen or a residue A; m and an are integers sufficient to provide polymer of weight averaged molecular weight ranging from about 400 to about 5000; m and n in residue A may each be the same or different from respective m and n in residue B; R is an —OX, where X is selected from the group consisting of hydrogen, alkali metal, alkaline earth metal, transition metal ammonium, alkyl amine, alkanolammonium residues and mixtures thereof; $R_1$, $R_2$, $R_3$ and $R_4$ are hydrogen, methyl, ethyl radicals or combinations thereof; and
   (ii) an effective amount of antibacterial agent for destroying microorganisms selected from the group consisting of diphenyl ethers, bis-biguanides, halogenated carbanilides and salicylamides.

2. A composition according to claim 1 wherein the molecular weight of the polymer ranges from about 600 to about 2500.

3. A composition according to claim 1 wherein the structure II is formed from monomers selected from the group consisting of acrylic, methacrylic, alpha-substituted acrylic, beta-carboxyalkyl acrylic acids or salts, and mixtures thereof.

4. A composition according to claim 1 wherein the structure III is formed from monomers selected from the group consisting of maleic, fumaric, mesaconic, citraconic acid residues including their anhydrides or salts, and mixtures thereof.

5. A composition according to claim 1 wherein the polymer is present in amounts ranging from about 0.1 to about 10% by weight.

6. A composition according to claim 1 wherein the relative molar ratio of structure II to structure III ranges from about 5:1 to about 1:5.

7. A composition according to claim 1 wherein the polymer is formed from a combination of acrylic acid or salt and maleic anhydride, its acid or salt and sodium hypophosphite.

8. A composition according to claim 7 wherein the molar ratio of total monomer to hypophosphite utilized to prepare the polymer ranges from about 40:1 to about 1:1.

9. A composition according to claim 1 wherein the diphenyl ether has the formula 1:

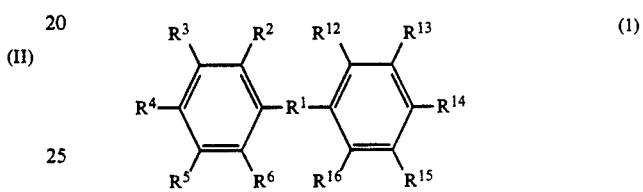  (1)

in which $R^1$ is oxygen, sulfur or an alkylene group of from one to six carbon atoms and each of $R^2$ through $R^6$ and $R^{12}$ through $R^{16}$ is hydrogen, hydroxyl or a halogen.

10. A composition according to claim 9 wherein formula 1 is 2,4,4'-trichloro-2'-hydroxydiphenyl ether.

11. A composition according to claim 1 wherein the bis-biguanides is of formula 2:

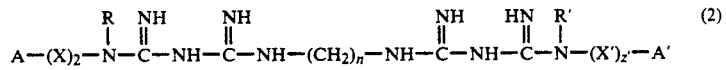  (2)

wherein A and A' each is selected from the group consisting of
   (1) a phenyl radical which optionally is substituted by an alkyl or alkoxy group containing from 1 to about 4 carbon atoms, a nitro group or a halogen atom;
   (2) an alkyl group containing from 1 to about 12 carbon atoms; or
   (3) alicyclic groups containing from 4 to about 12 carbon atoms;
X and X' each represent an alkylene radical containing from 1 to 3 carbon atoms;
z and z' each can be either 0 or 1:
R and R' each represent either hydrogen, an alkyl radical containing from 1 to about 12 carbon atoms or an aralkyl radical containing from 7 to about 12 carbon atoms;
n is an integer from 2 to 12 inclusive; and
wherein the polymethylene chain $(CH_2)_n$ may optionally be interrupted by a bridging unit selected from the group consisting of oxygen atoms, sulfur atoms and aromatic radicals.

12. A composition according to claim 11 wherein the bis-biguanides is chlorhexidine.

13. A composition according to claim 1 wherein the halogenated carbanilides are selected from the group consisting of 3,4,4'-trichlorocarbanilide; 3-trifluoromethyl-4,4'-dichlorocarbanilide; and 3,3',4-trichlorocarbanilide.

14. A composition according to claim 1 wherein the salicylamide has a formula (3):

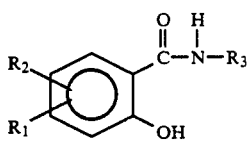
(3)

wherein the lipophilicity imparting substituents —$R_1$ and —$R_2$ which impart an octanol/water distribution function of about 3.0 to about 10 to the salicylamide are hydrogen, normal or branched chain or cyclic or fused ring polycyclic or non-fused ring polycyclic alkyl, alkenyl, alkynyl, aryl or heteroaryl groups optionally containing further substituents thereon, said —$R_1$ and —$R_2$ substituents comprising up to about 30 carbon atoms when taken together either attached directly to the phenyl ring provided with an amido and a hydroxyl group in an ortho orientation with respect to each other or attached to said phenyl ring through a

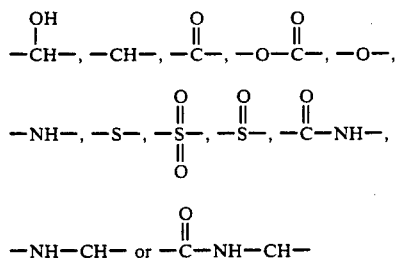

group with the proviso that—$R_1$ and $R_2$ are not both hydrogen and wherein—$R_3$ is selected from the group consisting of thiazol-2-yl, benzothiazol-2-yl and $R_4$-substituted phenyl wherein $R_4$ is selected from the group consisting of —OH,—COOH, the tautomeric pair

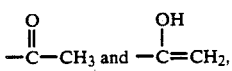

—$CH_2COOH$,—$COOCH_3$,—$COOC_2H_5$,—$CH_2COOCH_3$,—$CH_2COOC_2H_5$, —$NO_2$, and $CX_1X_2X_3$ wherein $X_1$, $X_2$ and $X_3$ are halogen atoms, with halogen atoms directly attached to any aromatic ring being absent in said salicylamides.

15. A composition according to claim 1 wherein the salicylamide has a formula 3a:

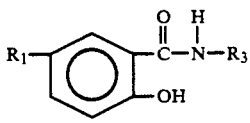
(3a)

wherein $R_1$ is n-decanoyl, and $R_3$ is p-nitrophenyl;
$R_1$ is n-octanoyl, and $R_3$ is p-trifluoromethylphenyl;
$R_1$ is a n-octanoyl, and $R_3$ is m-trifluoromethylphenyl;
$R_1$ is n-hexyl, and $R_3$ is p-nitrophenyl;
$R_1$ is n-butyl, and $R_3$ is m-trifluoromethylphenyl;
$R_1$ is n-nonanoyl, and $R_3$ is m-carbethoxyphenyl;
$R_1$ is a n-decanoyl, and $R_3$ is benzothiazol-2-yl;
$R_1$ is n-hexadecanoyl, and $R_3$ is thiazol-2-yl; and
$R_1$ is n-decanoyl, the—OH group is replaced by acryloyloxy and $R_3$ is p-nitrophenyl.

16. A composition according to claim 1 wherein the antibacterial agent is present in an amount from about 0.001 to about 10% by weight.

17. A method for controlling tartar and plaque formation comprising applying into an oral cavity a composition according to claim 1.

* * * * *